United States Patent
Obara et al.

(10) Patent No.: US 8,426,142 B2
(45) Date of Patent: Apr. 23, 2013

(54) IGA NEPHROPATHY TESTING METHOD AND TEST KIT

(75) Inventors: Takashi Obara, Ibaraki (JP); Sadaaki Mizoguchi, Ibaraki (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 201 days.

(21) Appl. No.: 12/995,489

(22) PCT Filed: May 29, 2009

(86) PCT No.: PCT/JP2009/059872
§ 371 (c)(1),
(2), (4) Date: Dec. 1, 2010

(87) PCT Pub. No.: WO2009/147998
PCT Pub. Date: Dec. 10, 2009

(65) Prior Publication Data
US 2011/0091915 A1    Apr. 21, 2011

(30) Foreign Application Priority Data
Jun. 2, 2008 (JP) ................................. 2008-144882

(51) Int. Cl.
*G01N 33/53* (2006.01)
(52) U.S. Cl.
USPC .......................................... 435/7.1; 436/518
(58) Field of Classification Search .................. None
See application file for complete search history.

(56) References Cited

U.S. PATENT DOCUMENTS

| | | | |
|---|---|---|---|
| 5,139,932 | A | 8/1992 | Cederholm et al. |
| 6,277,574 | B1 | 8/2001 | Walker et al. |
| 2007/0207464 | A1 | 9/2007 | Hart et al. |
| 2009/0117591 | A1 | 5/2009 | Izquierdo et al. |

FOREIGN PATENT DOCUMENTS

| | | |
|---|---|---|
| JP | 2592121 | 3/1997 |
| JP | 2-503714 | 11/1999 |
| JP | 2000-241431 | 9/2000 |
| JP | 2002-541787 | 12/2002 |
| JP | 2006-503591 | 2/2006 |
| WO | WO 88/08983 | 11/1988 |
| WO | WO 2004/038377 | 5/2004 |
| WO | 2007/003670 | 1/2007 |

OTHER PUBLICATIONS

Julian et al. (Electrophoresis 2007 vol. 28, p. 4469-4483;online publication Aug. 2007).*
Communication from European Patent Office for European Application No. 09758265.4 (Oct. 7, 2011).
Julian et al., "Uriary biomarkers of IgA nephropathy and other IgA-associated renal diseases," *World J. Urol* (2007) 25:467-476.
Machii et al., "Analysis of an Expanded Width of Albumin Fraction by Cellulose Acetate Membrane Electrophoresis in IgA Nephropathy Urine Before Treatment," *Journal of Clinical Laboratory Analysis* (2003) 17:37-43.
Matousovic et al., "IgA-containing immune complexes in the urine of IgA nephropathy patients," *Nephrol Dial Transplant* (2006) 21:2478-2484.
Cederholm et al., "Circulating complexes containing IgA and fibronectin in patients with primary IgA nephropathy", PNAS, 85:4865-4868 (1988).
Jelakovic et al., "Antibodies to Tamm-Horsfall protein in endemic nephropathy", Nephrology Dialysis Transplantation, 14:2645-2649 (1999).

\* cited by examiner

*Primary Examiner* — Jacob Cheu
(74) *Attorney, Agent, or Firm* — Fish & Richardson P.C.

(57) ABSTRACT

There is provided a renal disease testing method comprising a complex detection step of detecting a complex of human uromodulin and human IgA in a sample derived from urine collected from a subject. It is preferred that the renal disease testing method of the invention further comprises a determination step of assessing the whether the renal disease is IgA nephropathy based on the ratio of the amount of the complex detected in the complex detection step to the amount of urinary proteins in the sample. The renal disease testing method of the invention has good detection sensitivity and specificity, and can conveniently and safely assess the existence of a renal disease (preferably, IgA nephropathy).

16 Claims, 9 Drawing Sheets

C : PURIFIED Uromodulin
1 : URINE FROM PATIENT WITH IgA NEPHROPATHY
2 : URINE FROM PATIENT WITH IgA NEPHROPATHY
3 : URINE FROM PATIENT WITH IgA NEPHROPATHY

IGA NEPHROPATHY TESTING METHOD AND TEST KIT

TECHNICAL FIELD

The present invention relates to a method of detecting IgA nephropathy and a test kit.

BACKGROUND ART

IgA nephropathy is a disease that was reported by Berger, et al., in 1968, and is the most frequent kidney disease among chronic glomerulonephritis other than diabetic nephropathy (for example, see Non-Patent Document No. 1). IgA nephropathy is a disease with a poor long-term prognosis and it is estimated that about 25% of patients with terminal renal failure who are in need of dialysis treatment have IgA nephropathy as the original disease. Although there are methods for delaying the progress of IgA nephropathy, no therapeutic method of treating the disease has been found. Recently, however, a treatment method has been established by Hotta, et al., by which complete remission is achieved if the treatment is started at an early stage.

Meanwhile, according to the "Joint Committee of the Specified Progressive Diseases Investigative Research Division for Progressive Renal Diseases of the Ministry of Health and Welfare and the Japanese Society of Nephrology", while an analysis of urine (continuous microscopic hematuria, continuous or intermittent proteinuria, macroscopic hematuria) and a blood test (blood serum IgA value is 350 mg/dL or more) are employed as supplementary diagnostic criteria, confirmation of IgA precipitation in a glomerular mesangial area based on kidney biopsy is the only means for definite diagnosis of IgA nephropathy. However, as kidney biopsy requires hospitalization for a week or so and is a risky method accompanied by severe bleeding, the diagnosis rate is not necessarily high. Thus, a detection method by which early IgA nephropathy can be conveniently and safely diagnosed is needed.

Further, although methods such as those using an IgA-fibronectin complex are known as diagnosis methods for IgA nephropathy (for example, see Japanese Patent Application Laid-Open (JP-A) No. 2000-241431, Japanese Patent (JP-B) No. 2592121, and Cederholm et al., Proc. Natl. Acad. Sci., 85: 4865-8, 1988), until now no practical method has been developed.

DISCLOSURE OF THE INVENTION

Problems to be Solved by the Invention

An object of the invention is to provide an IgA nephropathy testing method and a test kit having good detection sensitivity and specificity which can conveniently and safely assess the existence of IgA nephropathy.

Means for Solving the Problems

As a result of extensive research and measuring the quantity of a complex of uromodulin and IgA in human urine, the inventors of the invention found that the complex was present in higher concentration in an IgA nephropathy patient compared to a healthy person or a patient having a renal disease other than IgA nephropathy, and therefore completed the invention.

Thus, the specific means for solving the problems above is shown below.

According to a first aspect of the invention, there is provided an IgA nephropathy testing method comprising a complex detection step of detecting a complex of human uromodulin and human IgA in a sample derived from urine collected from a subject. It is preferable that the complex detection step comprise bringing the sample into contact with an antibody against the human uromodulin and into contact with an antibody against human IgA. Furthermore, it is preferable that the method further comprise a step of obtaining the ratio of the amount of the complex detected in the complex detection step to the amount of urinary proteins in the sample derived from urine collected from the subject. It is more preferable that the method further comprise a determination step of assessing an existence of IgA nephropathy based on the ratio above.

According to a second aspect of the invention, there is provided a renal disease testing method comprising a complex detection step of detecting a complex of human uromodulin and human IgA in a sample derived from urine collected from a subject. It is preferred that the complex determination step comprises brining the sample into contact with an antibody against human uromodulin and an antibody against human IgA.

According to a third aspect of the invention, there is provided an IgA nephropathy testing method comprising a complex detection step of detecting a complex of human uromodulin and human IgA in a sample derived from urine collected from a subject, a first determination step of assessing the existence of a renal disease on the basis of at least one of an amount of the complex detected in the complex detection step or an amount of urinary proteins in the sample, and a second determination step of assessing whether the renal disease is IgA nephropathy based on the ratio of the amount of the complex detected in the complex detection step to the amount of urinary proteins in the sample.

The complex detection step of the invention is preferably an immunochemical method using an antibody against human uromodulin and an antibody against human IgA, and more preferably a sandwich method using the same.

According to a fourth aspect of the invention, there is provided a method of detecting a complex of human uromodulin and human IgA, which comprises a step of bringing the sample derived from urine collected from a subject into contact with an antibody against human uromodulin and an antibody against human IgA. It is preferable that the complex is detected by an immunochemical method using an antibody against human uromodulin and an antibody against human IgA. It is more preferable that the complex is detected by a sandwich method using the same.

Further, the subject is preferably a person who has developed a renal disease, a person who is suspected to have developed a renal disease, or a person who has a possibility of developing a renal disease. The renal disease is preferably IgA nephropathy.

According to a fifth aspect of the invention, there is provided a test kit for a renal disease that comprises at least an antibody against human uromodulin and an antibody against human IgA. The renal disease is preferably IgA nephropathy.

Effects of the Invention

According to the invention, an IgA nephropathy testing method and a test kit having good detection sensitivity and specificity which can conveniently and safely assess the existence of IgA nephropathy are provided.

BEST MODES FOR CARRYING OUT THE INVENTION

Figure 1:
FIG. 1 is a distribution chart showing the measured values of the IgA-uromodulin complex in urine which is detected by ELISA.

In the following, the exemplary embodiments of the invention will be specifically described. However, the scope of the invention is not limited thereto.

The renal disease testing method of the invention comprises a complex detection step of detecting a complex of human uromodulin and human IgA, from a sample derived from urine collected from a subject. By detecting the complex from the sample, a renal disease of the subject may be detected with good detection sensitivity and good specificity. In this context, the renal disease includes IgA nephropathy and renal diseases other than IgA nephropathy.

According to the invention, the sample may be urine itself which is collected from a subject or urine obtained after a treatment like dilution, concentration, and the like which is usually performed on collected urine. According to the invention, the preferred sample is a urine sample obtained by diluting urine collected from a human based on a general method.

Furthermore, the sample derived from urine collected from the subject may be obtained by brining the urine sample above into contact with an antibody against human uromodulin or into contact with an antibody against human IgA.

Human uromodulin (which, in the following, may be referred to simply as "uromodulin") is a glycoprotein derived from the kidney that has molecular weight of 85 kd. The uromodulin is known to bind to IL1 and TNF and to act to inhibit IL1, and is thought to have an anti-inflammatory effect. Furthermore, uromodulin is known to exist in large amounts in urine during pregnancy.

The protein moiety of uromodulin is known to be the same as the protein moiety of Tamm-Horsfall protein, which is the dominant glycoprotein in urine collected from a healthy person. However, nothing is known regarding the relationship between uromodulin and renal disease.

In the invention, the terms "human uromodulin" and "uromodulin" include uromodulin itself and Tamm-Horsfall protein.

The complex detection method is not specifically limited, and protein detection methods that are generally used in the art may be used. Preferably, the detection method is a method which allows quantification or semi-quantification of the complex that is to be detected. Examples include a method using an antibody that binds to the complex, ion exchange chromatography, and mass spectroscopy.

According to the invention, the apparatus which is used for the complex detection is not specifically limited, and it may be appropriately selected depending on a complex detecting method. Specific examples include an HPLC apparatus, an apparatus for mass spectrometry, an apparatus for electrophoresis (an apparatus for capillary electrophoresis, and the like), a full-automatic or semi-automatic apparatus for enzyme immunoassay, a cell washer, a full-automatic or semi-automatic apparatus for chemiluminescence immunoassay, an apparatus for detecting luminescence, a full-automatic or semi-automatic apparatus for electro-chemiluminescence immunoassay, an apparatus for optical measurement, a plate reader, a CCD camera, a full-automatic or semi-automatic apparatus for fluorescence immunoassay, an apparatus for fluorescence measurement, a full-automatic or semi-automatic apparatus for radioimmunoassay, a liquid scintillation counter, a coulter counter, an apparatus for measuring surface plasmon, and an apparatus for blotting and a densitometer.

From the viewpoint of sensitivity, specificity and convenience of detection, in the invention, an immunochemical method using an antibody binding to the complex is preferable. As for the antibody against the complex, it is not specifically limited if it can recognize the complex with immunity specificity and bind to the complex. Examples include an antibody which recognize binding site of uromodulin and IgA in the complex, an antibody which recognize uromodulin moiety in the complex, and an antibody which recognize IgA moiety in the complex.

In the specification of the invention, the term "antibody against the complex" may have the same definition as the general meaning of antibody like in "antibody which recognizes the complex" and "antibody which binds to the complex." Specifically, the "antibody against the complex" binds to at least part of the complex consisting of human uromodulin and human IgA to form a new complex. Herein below, the same holds true for the expressions the "antibody against human uromodulin" and the "antibody against human IgA."

As for the immunochemical method used in the invention, a method that is generally used in the art may be used without any limitation. Specific examples include enzyme immunoassay (ELISA), chemiluminescence immunoassay, electrochemiluminescence immunoassay, absorbance determination, a fluorescent antibody method, radioimmunoassay (RIA), surface plasmon resonance, Western blot and dot blot. From the viewpoint of sensitivity, specificity and convenience of detection, it is preferable to use enzyme immunoassay (ELISA) in the invention.

As for an immunochemical method used in the invention, from the viewpoint of specificity and convenience, a sandwich method using an antibody that recognizes and binds to human uromodulin in the complex and an antibody that recognizes and binds to human IgA in the complex is preferable.

The sandwich method may be carried out as follows, for example. An antibody that binds to the complex (i.e., a primary antibody) is immobilized on a carrier like a plate, and the like. Generally, in order to block a non-specific binding site in the plate or the like, a blocking process is performed by using a protein such as casein or a surfactant. Subsequently, a sample derived from urine or a test sample is added and incubated. After washing the plate, as an antibody which binds to the complex, a labeled secondary antibody is added followed by incubation. Then, by washing the plate or the like and detecting the label, the process may be carried out.

From the viewpoint of detection sensitivity and specificity, it is preferable that two kinds of antibodies selected from the antibodies that bind to the complex are used as the primary antibody and the secondary antibody described above. It is more preferable that the antibody against human uromodulin is used as one of the primary antibody and the secondary antibody described above while the antibody against human IgA is used as the other antibody. It is still more preferable that the antibody against human uromodulin is used as the primary antibody while the antibody against human IgA is used as the secondary antibody.

According to the invention, the antibody that binds to the complex may be either a polyclonal antibody or a monoclonal antibody. From the viewpoint of specificity for detecting a renal disease, a monoclonal antibody is preferable.

The antibody that binds to the complex may be produced according to a method generally performed in the art.

The polyclonal antibody against human uromodulin may be produced according to a general producing method used in the art. It may be obtained as follows, for example. An animal such as a rabbit or a goat is immunized with uromodulin to obtain blood serum, which is then purified by ammonium sulfate precipitation, Protein A column, Protein G column, DEAE ion exchange chromatography, an affinity column to which uromodulin is attached, or the like for the production.

According to the invention, the antibody having higher specificity to human uromodulin, from which antibodies that bind to antigens other than human uromodulin are removed by a general method used in the art, for example, an absorption process, and the like is preferable.

Furthermore, for producing the monoclonal antibody against human uromodulin, a small animal such as a mouse is immunized with uromodulin, then the spleen is harvested from the mouse and homogenized to isolate the cells, which are then fused with a mouse myeloma cells by using a reagent such as polyethylene glycol and from the resulting fused cells (i.e., hybridoma) a clone producing an antibody that binds to human uromodulin is selected. Subsequently, the selected hybridoma is introduced to an abdominal cavity of a mouse, and the monoclonal antibody that is obtained from the ascites recovered from the same animal is purified by ammonium sulfate precipitation, Protein A column, Protein G column, DEAE ion exchange chromatography, an affinity column to which uromodulin is attached, or the like.

With respect to the antibody against uromodulin, a commercially available anti-human Tamm-Horsfall protein antibody and anti-human uromodulin antibody may be used.

Furthermore, the antibody against human uromodulin may be any of an antibody derived from a small animal such as a mouse as obtained above, a chimeric antibody, a humanized antibody, a fully human antibody, or the like.

As for the antibody against human IgA, it is not specifically limited so long as it is an antibody capable of binding to IgA in the complex. It may be any one that recognizes the H chain, the J chain, the secretory component, or the like of human IgA.

Furthermore, the antibody against human IgA may be either a polyclonal antibody or a monoclonal antibody. However, from the viewpoint of detection specificity for the complex, a monoclonal antibody against human IgA is preferable.

The monoclonal antibody against human IgA may be produced by using human IgA as an antigen in the same manner as the antibody against human uromodulin. Furthermore, as for the antibody against human IgA, a commercially available anti-human IgA antibody may be used.

Still furthermore, the antibody against human IgA may be any of an antibody derived from a small animal such as a mouse as obtained in the above, a chimeric antibody, a humanized antibody, a fully human antibody, or the like.

As for the label, any label well known in the art may be used without specific limitation. Examples include an enzyme, a chemiluminescent substance, an electro-chemiluminescent substance, a radioactive substance, and the like.

According to the invention, from the viewpoint of detection sensitivity and convenience, it is preferable to use an enzyme as the label.

The enzyme is not specifically limited so long as it is an enzyme that can be quantified by a physical or a chemical method. Examples include an enzyme such as alkaline phosphatase, horseradish peroxidase (HRP) and luciferase.

Furthermore, a method of detecting the label is not specifically limited so long as it is a method that allows for quantification or semi-quantification of the label, and it may be appropriately selected depending on type of the label. Examples include absorbance, luminescence intensity, fluorescence intensity, and radioactivity count.

Based on the quantification or semi-quantification of the label, quantification or semi-quantification of the complex may be achieved.

When the complex detection step of the invention is carried out with absorbance determination for detecting the label using enzyme immunoassay (ELISA), an example of a measurement apparatus for the complex detection that is preferably used in the invention is an absorbance determination apparatus that allows the measurement of absorbance of a chromophore generated by the label that is bound to the complex and is equipped with a sample loading part in which a sample containing the chromophore generated by the label is loaded, a light irradiating part in which light is irradiated onto the sample, and a light quantity measuring part in which at least one of reflected light or transmitted light is collected from the sample and the collected light quantity is measured.

According to the invention, by irradiating light onto the chromophore that is generated by the label bound to the complex of human uromodulin and human IgA in a test sample (i.e., a sample derived from urine collected from a subject) via the light irradiating part and quantifying the absorbance of the chromophore through the light quantity measuring part, the content of the complex of human uromodulin and human IgA in the sample may be measured.

When the complex detection step of the invention is carried out by measurement of the light emitted from a sample for detecting the label using electrochemiluminescence (ECL), an apparatus that allows the measurement of light emitted from the label bound to the complex itself or from the substrate in a reaction liquid is used as a measurement apparatus for the complex detection that is preferably used in the invention, and examples include a measurement apparatus equipped with a sample loading part in which a sample containing the label is loaded and a light quantity measuring part in which emitted light is collected from the sample and the collected light quantity is measured.

According to the invention, by quantifying the light emitted from a sample containing the label that is bound to the complex of human uromodulin and human IgA contained in a test sample via a light quantity measuring part, the content of the complex of human uromoduline and human IgA contained in a test sample may be measured.

The renal disease testing method of the invention preferably comprises a step to assess the existence of a renal disease based on the detected amount of the complex contained in a sample derived from urine. As for the detected amount of the complex, so long as it is the concentration of the complex contained in a sample derived from urine or the quantitative or a semi-quantitative value corresponding thereto, it may be used without specific limitation. Examples include a measurement value obtained by directly measuring the detected amount of the complex, a measurement value obtained by indirectly measuring the detected amount of the complex via detection of the label, and the like.

Furthermore, when IgA nephropathy is examined by the renal disease testing method of the invention, it is preferable that the detected amount of the complex used for assessing an existence of IgA nephropathy is the ratio of the detected amount of the complex to the total amount of urinary proteins in the sample derived from urine collected from a subject. The ratio may be any value that is obtained by dividing the measured value of the detected amount of the complex by the measured value of the total amount of urinary proteins in the sample derived from urine collected from a subject, or the detected amount of the complex that is obtained as a relative value compared to the total amount of urinary proteins. By carrying out the determination based on this ratio, IgA nephropathy may be determined with higher sensitivity and specificity.

Furthermore, regarding the sample derived from urine collected from a subject from which the total amount of urinary proteins is measured, as long as it is obtained from the same subject, it may be a sample different from the sample derived from urine that is used for the detection of the complex as described above.

The determination step of the renal disease testing method of the invention preferably comprises a step of comparing the detected amount of the complex of human uromodulin and human IgA in a sample derived from urine collected from a subject with the detected amount of the complex in samples derived from urine of healthy persons as a control, and a step of correlating a case in which the detected amount of the complex in the sample derived from urine collected from a subject is higher than the detected amount of the complex in the sample derived from urine of healthy persons as a control, with the existence of a renal disease.

Herein, the healthy persons as a control mean individuals who have previously been determined to have no occurrence of a renal disease. In addition, the expression "detected amount is higher" indicates that the detected amount of the complex derived from a subject is higher than the normal detected amount (i.e., a cut-off value) that is established in order to distinguish healthy persons from patients having a renal disease.

The cut-off value may be established by, for example, subjecting the detected amount of the complex in a sample group derived from urine of patients having a renal disease and the detected amount of the complex in a sample group derived from urine of healthy persons as a control to ROC analysis, or the like. ROC analysis is an analytical method allowing, for example, the evaluation of detectability and diagnosability of a method of examining a disease. It is an analysis method described in Journal of The Japan Society for Clinical Laboratory Automation, "Manual for evaluation of diagnostic usefulness of clinical test" Ver. 1.3 (2004.9.1), Vol. 29 Suppl. 1 (Serial Number 154) (published on Sep. 1, 2004), for example.

Furthermore, the cut-off value may be defined as a value that is obtained by adding two or three times of the standard deviation to a mean detection level in healthy persons, or it may be suitably defined as a value which satisfies both the sensitivity (detection ratio) and specificity (i.e., low false positive ratio) in balance.

Examples of the renal disease in the invention include IgA nephropathy (IgAN), membranous nephropathy (MN), lupus nephropathy (SLE), focal glomerulosclerosis (FGS), minimal change nephritic syndrome (MCNS), diabetic nephropathy (DMN), amyloidosis, hereditary nephropathy (Alport), burnt-out IgA nephropathy (spontaneously remitted state of IgA nephropathy), membranoproliferative glomerulonephritis (MPGN), nephritis related with anti-neutrophil cytoplasmic antibody (ANCA), thin basement membrane disease (TBMD) nephrosclerosis, and the like.

According to the renal disease testing method of the invention, by detecting the complex in urine, various renal diseases including IgA nephropathy may be detected.

The IgA nephropathy testing method of the invention is characterized in that it comprises a complex detection step of detecting a complex of human uromodulin and human IgA in a sample derived from urine collected from a subject, a determination step of assessing the existence of a renal disease based on the amount of the complex detected in the complex detection step or the amount of urinary proteins in the sample derived from urine collected from a subject, and a determination step of assessing whether the renal disease is IgA nephropathy based on the ratio of the amount of the complex detected in the complex detection step to the amount of urinary proteins in the sample derived from urine collected from a subject.

By assessing the existence of IgA nephropathy based on the ratio of the detected amount of the complex to the total amount of urinary proteins in the sample derived from urine, the existence of IgA nephropathy may be conveniently and safely determined with high sensitivity and high specificity, even at an early stage of the disease at which complete remission may be obtained by therapeutic intervention.

The complex detection step according to the invention is the same as the complex detection step for the renal disease testing method described above.

Furthermore, as for the method of detecting an amount of urinary proteins, if it allows the measurement of the total amount of urinary proteins in the sample derived from urine, a method for detecting proteins in a sample derived from urine that is generally performed in the art may be used without specific limitation. For example, the method described in the literature ("Revised edition of outlines for clinical test, 32nd edition" by Kanai Mitsumasa et al., pages 173-174, 2005) may be used.

With respect to the first determination step of the invention, assessing the existence of a renal disease based on the amount of the complex detected in the complex detection step is the same as the determination step of the renal disease testing method described above.

Furthermore, the step of assessing the existence of a renal disease based on the amount of urinary proteins in the sample derived from urine preferably comprises a step of correlating the case in which the amount of urinary proteins in a sample derived from urine collected from a subject is higher than the normal detected amount (i.e., a cut-off value) that is established in order to distinguish patients having a renal disease from normal persons, with the existence of a renal disease.

Herein, the normal detected amount of urinary proteins may be defined by a general method.

The secondary determining step of the invention preferably comprises a step of comparing the ratio of the detected amount of the complex in a sample derived from urine collected from a subject to the total protein amount in the sample (i.e., the complex/total protein) with the ratio of the detected amount of the complex in a sample derived from urine collected from subjects who have a renal disease other than IgA nephropathy as a control to the total protein amount in the sample, and correlating the case in which the ratio of the detected amount of the complex in a sample derived from urine collected from a subject to the total protein amount in the sample is higher than the ratio of the detected amount of the complex in a sample derived from urine collected from subjects who have a renal disease other than IgA nephropathy as a control to the total protein amount in the sample, with the existence of IgA nephropathy.

Herein, the higher ratio means that the detected amount ratio of the complex derived from a subject is higher than the cut-off value that is determined to distinguish IgA nephropathy from renal diseases other than IgA nephropathy.

The cut-off value may be established to have the same value as the cut-off value described in detail above for the renal disease testing method. However, from the viewpoint of detection specificity, the cut-off value is preferably assessed based on the results of ROC analysis.

According to the IgA nephropathy testing method of the invention, the detected amount of the complex and total protein amount in urine are measured and IgA nephropathy may be assessed based on the ratio of the detected amount of the complex to the total protein amount. Therefore, it is a convenient and safe method of detecting IgA nephropathy.

The method of detecting the complex of human uromodulin and human IgA of the invention comprises a step of bringing the sample derived from urine collected from a subject into contact with an antibody against human uromodulin and an antibody against human IgA. As a result, the complex of human uromodulin and human IgA may be detected with high sensitivity and high specificity.

Those described in detail above regarding the complex detection step for the renal disease testing method may be also applied to the method of detecting the complex of this invention.

Furthermore, the subject is preferably a person who has developed a renal disease, a person who is suspected to have developed a renal disease, or a person who has the possibility of developing a renal disease. Herein, a person who has the possibility of developing a renal disease means a person who is neither a person who has developed a renal disease nor a person who is suspected to have developed a renal disease. Still furthermore, the renal disease is more preferably IgA nephropathy.

The test kit for a renal disease of the invention is characterized in that it comprises at least one antibody against human uromodulin and at least one antibody against human IgA. By detecting the complex of human uromodulin and human IgA using the antibody against human uromodulin and the antibody against human IgA, the renal disease may be detected with good detection sensitivity and good specificity.

It is preferable that the test kit for a renal disease of the invention further comprises an instruction which describes brining the sample derived from urine collected from a subject into contact with the antibody against human uromodulin and the antibody against human IgA to detect the complex of human uromodulin and human IgA, and correlating the detected amount with an existence of a renal disease.

Furthermore, the test kit for a renal disease of the invention may be preferably used for assessing an existence of IgA nephropathy.

Disclosure of the Japanese Patent Application No. 2008-144882 is incorporated by reference herein in its entirety.

All publications, patent applications, and technical standards that are described in the specification are herein incorporated by reference to the same extent as if each individual publication, patent application, or technical standard was specifically and individually indicated to be incorporated by reference.

EXAMPLES

In the following, the present invention is explained specifically with reference to examples. However, the invention is not limited by the examples. Furthermore, unless specifically mentioned otherwise, "%" represents mass percentage.

Example 1

Detection of Renal Disease

—Detection of IgA-Uromodulin Complex in Urine Based on ELISA—

Anti-human Tamm-Horsfall protein antibody (manufactured by Cedarlane Laboratories) was purified by PROSEP-A (manufactured by Millipore Corp.) followed by dialysis against 50 mM Tris/HCl (pH 7.5) and 0.15 M NaCl. The purified antibody was diluted to the concentration of 5 µg/ml to 10 µg/ml by using 50 mM Tris/HCl (pH 7.5) and 0.15 M NaCl, and then added to PolySorp cups (manufactured by NUNC) (50 μl/well). The cups were placed in a humid box and coating was carried out overnight at 4° C. After the coating, they were washed three times with the washing solution (50 mM Tris/HCl (pH 7.5), 150 mM NaCl and 0.01% Tween20) followed by addition of the blocking solution (50% N102 (manufactured by NOF Corp.), 25 mM Tris/HCl (pH 7.5), 75 mM NaCl and 2% Block Ace (manufactured by Dainippon Sumitomo Pharma Co., Ltd.)) (150 μl/well). Thereafter, the blocking was carried out at room temperature for 2 hours or at 4° C. for one day or more (herein below, referred to as "anti-Tamm-Horsfall cups").

The anti-Tamm-Horsfall cups were washed three times with the washing solution (50 mM Tris/HCl (pH 7.5), 150 mM NaCl and 0.01% Tween20) and added with urine samples, which were obtained by 50 times dilution using a sample dilution solution (50% N102 (manufactured by NOF Corp.), 50 mM Tris/HCl (pH 7.5), 150 mM NaCl and 2% Block Ace (manufactured by Dainippon Sumitomo Pharma Co., Ltd.)), in an amount of 50 μl/well for the reaction at room temperature for 1 hour. After washing three times with the washing solution (50 mM Tris/HCl (pH 7.5), 150 mM NaCl and 0.01% Tween20), HRP-GOAT Anti-Human IgA (manufactured by Zymed Labs) which was diluted 3,000 times with Can Get Signal 2 (manufactured by Toyobo Inc.) was added in an amount of 50 μl/well, and the reaction was carried out at room temperature for 1 hour. After washing three times with the washing solution, 3,3',5,5'-Tetramethylbenzidine (TMB) Liquid Substrate System for ELISA (manufactured by Sigma Chemical Corporation) was added in an amount of 100 μl/well followed by reaction at room temperature for 30 minutes. After adding 0.5 M $H_2SO_4$ (100 μl/well) to terminate the reaction, OD (450 to 650 nm) was measured. Measurement results obtained from 147 cases of patients having a renal disease including 95 cases of patients having IgA nephropathy and 20 cases of healthy persons (normal people) are shown in FIG. 1.

By comparing the value obtained after subtraction of blank, results showing a clear differentiation of 147 cases of patients having a renal disease including 95 cases of patients having IgA nephropathy from 20 cases of healthy persons (normal people) were obtained.

Figure 2:
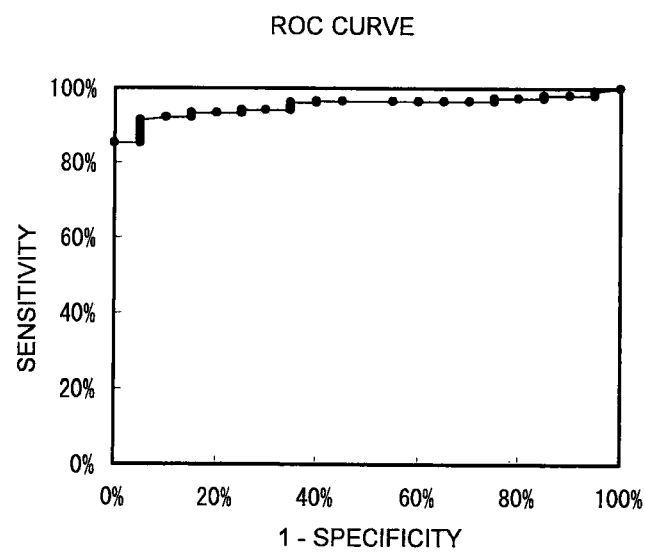
FIG. 2 is a diagram showing the results obtained from ROC analysis of the measured values of IgA-uromodulin complex in urine which is detected by ELISA.

Furthermore, ROC analysis was carried out for 147 cases of patients having a renal disease and 20 cases of healthy persons. The ROC curve is shown in FIG. 2. The cut-off value calculated from the ROC curve was 0.066. The positive response ratio in 147 cases of patients having a renal disease and 20 cases of healthy persons, which was determined from the cut-off value, is shown in Table 1. As shown in Table 1, there were 134 cases showing a positive response (91.2%) out of 147 cases of patients having a renal disease compared to 1 case showing a positive response (5%) out of 20 cases of healthy persons, thus two groups can be clearly distinguished from each other. The sensitivity was 91.2%, specificity degree (specificity) was 95%, and diagnosis efficiency was 91.6%.

TABLE 1

|  | Patient having a renal disease | Healthy person |
| --- | --- | --- |
| Number of samples | 147 | 20 |
| Number of positive response | 134 | 1 |
| Positive response ratio | 91.2% | 5.0% |

<Detection of IgA Nephropathy>

Figure 3:
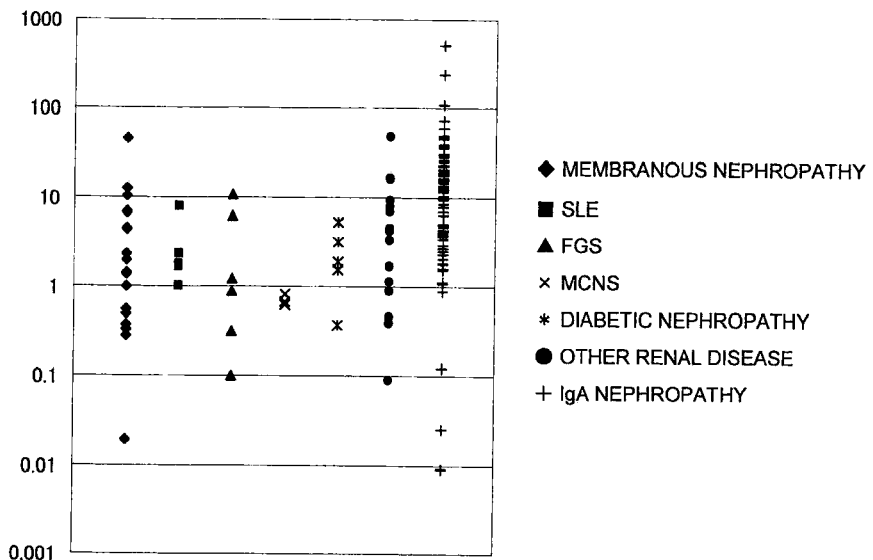
FIG. 3 is a distribution chart showing the measured values of the IgA-uromodulin complex in urine which is detected by ELISA, the measured values being corrected against the concentration of urinary proteins.

Next, for the samples exhibited color development values higher than the cut-off value, urinary proteins concentration in urine was quantified based on a pyrogallol red method. The detection amount of the complex obtained from the above was divided by the urinary protein concentration, and then the detection amount of the complex per amount of the urinary protein was calculated. The results are shown in FIG. 3. By comparing the detected amount of the complex per amount of the urinary proteins, the results demonstrating that 86 cases of patients having IgA nephropathy can be clearly distinguished from 47 cases of patients having a renal disease other than IgA nephropathy were obtained.

Figure 4:
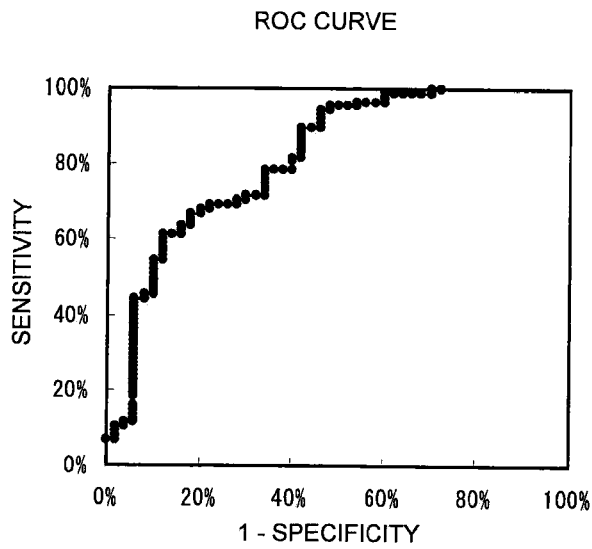
FIG. 4 is a diagram showing the results obtained from ROC analysis of the measurement values of the IgA-uromodulin complex in urine which is detected by ELISA, in which the measured values are corrected against the concentration of urinary proteins.

Furthermore, as a result of carrying out ROC analysis for 86 cases of patients having IgA nephropathy and 47 cases of patients having a renal disease other than IgA nephropathy, the ROC curve shown in FIG. 4 was obtained. The cut-off value calculated from the ROC curve was 6.5. The positive response ratio in 86 cases of patients having IgA nephropathy and 47 cases of patients having a renal disease other than IgA nephropathy, which was determined from the cut-off value, is shown in Table 2. As shown in Table 2, there were 62 cases showing a positive response (72.1%) out of 86 cases of patients having IgA nephropathy compared to 13 cases showing a positive response (27.7%) out of 47 cases of patients having a renal disease other than IgA nephropathy, thus two groups can be clearly distinguished from each other. The sensitivity was 72.1%, specificity degree was 72.3%, and diagnosis efficiency was 72.2%.

TABLE 2

|  | IgA nephropathy | Renal disease other than IgA nephropathy |
| --- | --- | --- |
| Number of samples | 86 | 47 |
| Number of positive response | 62 | 13 |
| Positive response ratio | 72.1% | 27.7% |

Example 2

Detection of Renal Disease

—Detection of IgA-Uromodulin Complex in Urine Based on Electrochemiluminescence (ECL)—

1 ml of Dynabeads M-450 Epoxy (manufactured by Invitrogen Corporation) (30 mg/ml) was trapped with magnets, and washed five times with 1 ml of PBS-1 (10 mM potassium phosphate buffer, 150 mM NaCl, pH 7.8). Subsequently, 1 ml of a solution of a purified antibody against anti-human Tamm-Horsfall protein (manufactured by Cedarlane Laboratories), which had been dialyzed against the PBS-1 and prepared to have the concentration of 0.2 mg/ml, was added to the beads trapped with magnets followed by mixing at 25° C. for 20 hours.

Subsequently, the beads obtained from the above were trapped with magnets, washed with 1 ml of the PBS-1, added with 50 mM Tris-HCl buffer (pH 7.5) including 1% BSA and 150 mM NaCl, and then mixed at room temperature for 2 hours. The beads were trapped with magnets, washed five times with 1 ml of the PBS-1, and then suspended in 50 mM Tris-HCl buffer (pH 7.5) including 0.1% BSA and 150 mM NaCl (herein below, referred to as "anti-Tamm-Horsfall bound beads").

24.3 μg of Ruthenium complex (manufactured by Igen) and 1.425 mg of goat anti-human IgA (manufactured by Cappel Labs) were mixed under lightproof condition at room temperature for 30 minutes. After adding 25 μl of 2 M glycine/PBS-1, the resultant was mixed under lightproof condition at room temperature for 10 minutes, and filtered through a Sephadex G-25 column. Consequently, the fractions containing the antibody against anti-human IgA to which the ruthenium complex is bound were pooled (herein below, referred to as an "anti-IgA ruthenium labeled antibody").

Figure 5:
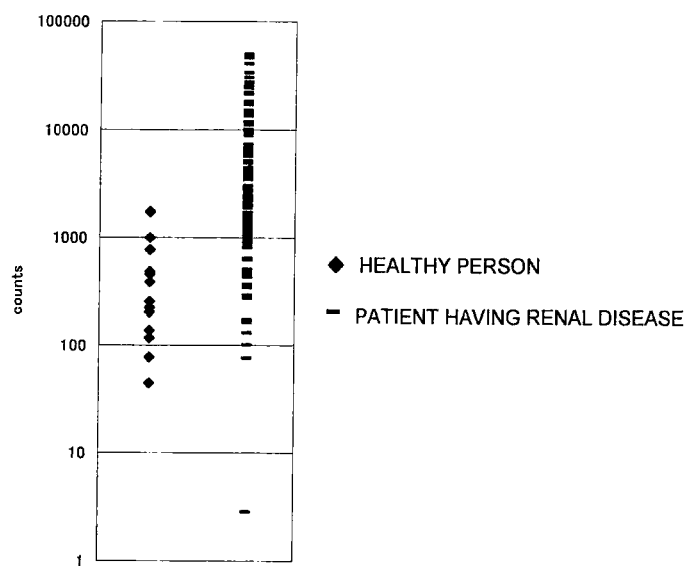
FIG. 5 is a distribution chart showing the measured values of the IgA-uromodulin complex in urine which is detected by ECL.

The anti-Tamm-Horsfall bound beads (30 mg/ml) were diluted 60 times (0.5 mg/ml) using a sample dilution solution (50% N102 (manufactured by NOF Corp.), 50 mM Tris/HCl (pH 7.5), 150 mM NaCl and 2% Block Ace (manufactured by Dainippon Sumitomo Pharma Co., Ltd.)). Further, the anti-IgA ruthenium labeled antibody was diluted with Can Get Signal 2 (manufactured by Toyobo Inc.) to have the concentration of 0.5 µg/ml. Each of the anti-Tamm-Horsfall bound beads which had been diluted 60 times and the anti-IgA ruthenium labeled antibody prepared to have concentration of 0.5 µg/ml were separately set in their own specific holder. To the reaction tubes, 200 µl of the sample dilution solution was added and 5 µl of each sample was added separately thereto followed by mixing and stirring. To the rack for specific reaction tube, the reaction tube was inserted, the reagents and the sample were placed in an automatic electrochemiluminescence measuring apparatus (PICOLUMI series, manufactured by Sanko Junyaku Co., Ltd.), and the autonomic measurement was performed under reaction condition including 9 minutes for a first reaction and 9 minutes for a second reaction. The results obtained from 128 cases of patients having a renal disease including 88 case of patients having IgA nephropathy and 19 cases of healthy persons are shown in FIG. 5.

By comparing the value obtained by subtraction of blank from the measured count value, results showing a significant difference between 128 cases of patients having a renal disease including 88 cases of patients having IgA nephropathy and 19 cases of healthy persons were obtained.

Figure 6:
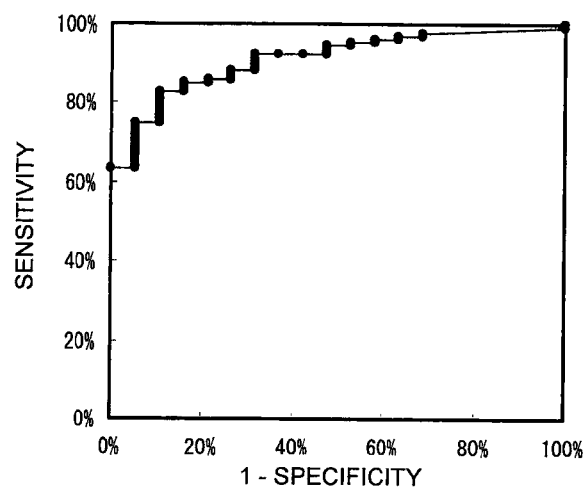
FIG. 6 is a diagram showing the results obtained from ROC analysis of the measured values of the IgA-uromodulin complex in urine which is detected by ECL.

Furthermore, as a result of carrying out ROC analysis for 128 cases of patients having a renal disease including 88 cases of patients having IgA nephropathy and 19 cases of healthy persons, the ROC curve shown in FIG. 6 was obtained. The cut-off value calculated from the ROC curve was 510.3. The positive response ratio in 128 cases of patients having a renal disease including 88 cases of patients having IgA nephropathy and 19 cases of healthy persons, which was determined from the cut-off value, is shown in Table 3. As shown in Table 3, there were 109 cases showing a positive response (85.2%) out of 128 cases of patients having a renal disease compared to 3 cases showing a positive response (15.8%) out of 19 cases of healthy persons, thus two groups can be clearly distinguished from each other. The sensitivity was 85.2%, specificity degree was 84.2%, and diagnosis efficiency was 85.0%.

TABLE 3

|  | Patient having a renal disease | Healthy person |
|---|---|---|
| Number of samples | 128 | 19 |
| Number of positive response | 109 | 3 |
| Positive response ratio | 85.2% | 15.8% |

<Detection of IgA Nephropathy>

Figure 7:
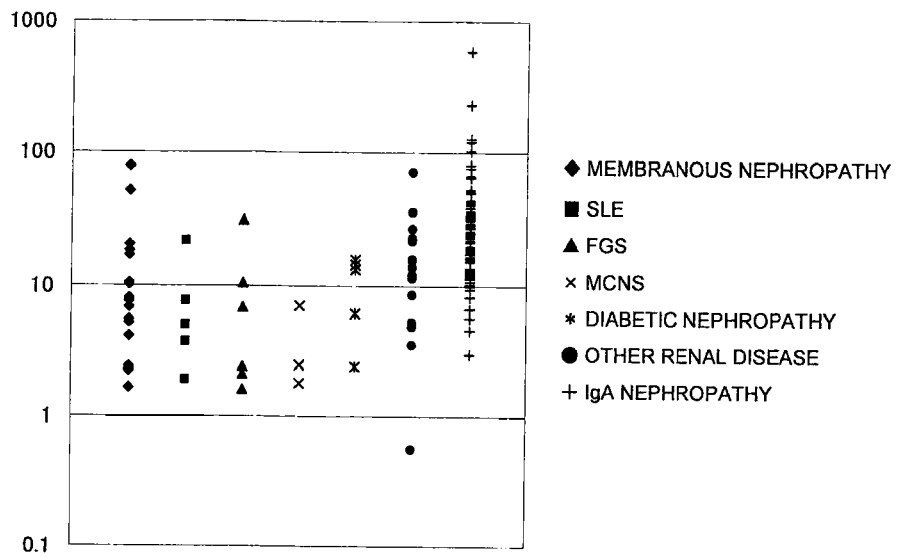
FIG. 7 is a distribution chart showing the measured values of the IgA-uromodulin complex in urine which is detected by ECL, in which the measured values are corrected against the concentration of urinary proteins.

Next, for the samples in which the values obtained by subtraction of the blank from the measured count value were the cut-off value or more, protein concentration in urine was quantified based on a pyrogallol red method. The detected amount of the complex, which has been detected from the above, was divided by the urinary protein concentration, and then the detected amount of the complex per amount of the urinary proteins was calculated. The results are shown in FIG. 7. It was found from FIG. 7 that 77 cases of patients having IgA nephropathy can be clearly distinguished from 32 cases of patients having a renal disease other than IgA nephropathy.

Figure 8:
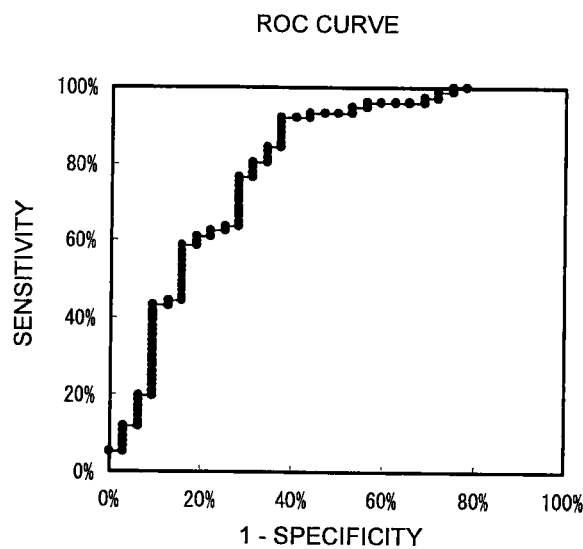
FIG. 8 is a diagram showing the results obtained from ROC analysis of the measured values of the IgA-uromodulin complex in urine which is detected by ECL, in which the measured values are corrected against the concentration of urinary proteins.

Furthermore, as a result of carrying out ROC analysis for 77 cases of patients having IgA nephropathy and 32 cases of patients having a renal disease other than IgA nephropathy, the ROC curve shown in FIG. 8 was obtained. The cut-off value calculated from the ROC curve was 39.525. The positive response ratio in 77 cases of patients having IgA nephropathy and 32 cases of patients having a renal disease other than IgA nephropathy, which was determined from the cut-off value, is shown in Table 4. As shown in Table 4, there were 58 cases showing a positive response (75.3%) out of 77 cases of patients having IgA nephropathy compared to 9 cases showing a positive response (28.1%) out of 32 cases of patients having a renal disease other than IgA nephropathy, thus two groups can be clearly distinguished from each other. The sensitivity was 75.3%, specificity degree was 71.9%, and diagnosis efficiency was 74.3%.

TABLE 4

|  | IgA nephropathy | Renal disease other than IgA nephropathy |
|---|---|---|
| Number of samples | 77 | 32 |
| Number of positive response | 58 | 9 |
| Positive response ratio | 75.3% | 28.1% |

Example 3

Analysis of Uromodulin Contained in the Uromodulin-IgA Complex in Urine Based on Western Blot Method 1 ml of Dynabeads M-450 Epoxy (manufactured by Invitrogen Corporation) (30 mg/ml) were trapped with magnets, and washed three times with 1 ml of the PBS-1 (10 mM potassium phosphate buffer, 150 mM NaCl, pH 7.8). 1 ml of a solution of an antibody against anti-human IgA (manufactured by Cappel Labs) that had been dialyzed against the PBS-1 and prepared to have the concentration of 0.2 mg/ml was added to the beads trapped with magnets and mixed for a day and night at 25° C.

The beads obtained from the above were trapped with magnets, washed with 1 ml of the PBS-1, added with 50 mM Tris-HCl buffer (pH 7.5) containing 1% BSA and 150 mM NaCl, and then mixed at 4° C. for a day and night. The beads were trapped with magnets, washed three times with 1 ml of the PBS-1, and then suspended in 50 mM Tris-HCl buffer (pH 7.5) containing 0.1% BSA and 150 mM NaCl (herein below, referred to as "anti-IgA bound beads").

Similarly, 1 ml of Dynabeads M-450 Epoxy (30 mg/ml) were trapped with magnets, washed three times with 1 ml of the PBS-1, added with 50 mM Tris-HCl buffer (pH 7.5) containing 1% BSA and 150 mM NaCl to the beads trapped with magnets, and then mixed at 4° C. for a day and night. The beads were trapped with magnets, washed three times with 1 ml of the PBS-1, and then suspended in 50 mM Tris-HCl buffer (pH 7.5) containing 0.1% BSA and 150 mM NaCl (herein below, referred to as "BSA bound beads").

2.5 ml of 1 M Tris-HCl buffer (pH 7.5) and 1.5 ml of 5 M NaCl were added to 45 ml of a urine sample. 0.25 ml of the anti-IgA bound beads or the BSA bound beads were further added and the mixture was mixed at 4° C. for a day and night. Each bead was trapped with magnets, washed five times with 50 ml to 1 ml of the PBS-1, added with 0.5 ml of 0.1 M citrate buffer (pH 3) and the mixture was stirred at room temperature for 30 minutes. The beads were trapped with magnets. The supernatant was recovered, dialyzed against PBS-1 (1/10 concentration) and 0.01% NaN$_3$, and concentrated to about 10× concentration by centrifuge to prepare the protein solution.

3 µl of the protein solution prepared from the above was subjected to SDS-PAGE, and then blotted on a nitrocellulose filter (trade name: BA85, manufactured by Schleicher & Schuell Bioscience GmbH). The filter was immersed in the blocking solution (50 mM Tris-HCl (pH 7.5), 150 mM NaCl, 5% skim milk, 0.01% Tween20, and 0.1% NaN$_3$) and shaken overnight at 4° C. After that, the blocking solution was exchanged with fresh one. The anti-uromodulin antibody (anti-human Tamm-Horsfall protein monoclonal antibody (manufactured by Cedarlane Laboratories, Ltd.)) was added as a primary antibody at 1/1,000 concentration, shaken at room temperature for 2 hours and washed three times with the washing solution. Subsequently, to the washing solution, HRP-labeled anti-mouse IgG (manufactured by Zymed Laboratories, Inc.) was added as a secondary antibody at 1/1,000 concentration, shaken at room temperature for 1 hour and washed three times with the washing solution. Then, the color developing solution (8.3 mM Tris-HCl (pH 6.5), 125 mM NaCl, 0.05% 4-Chloro-1-Naphtol and 0.01% H$_2$O$_2$) was added thereto for color development.

Figure 9:
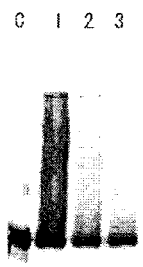
FIG. 9 shows the results of western blotting in of proteins which bound to beads including anti-IgA antibody.

Results obtained from the Western blot analysis of the protein which was bound to the anti-IgA bound beads are shown in FIG. 9. In FIG. 9, lane C corresponds to migration of purified uromodulin (10 µg) and lane 1 to 3 correspond to migration of the urinary proteins from patients having IgA nephropathy which bound to the anti-IgA bound beads.

From every test samples derived from patients having IgA nephropathy, a strong uromodulin band was observed. Thus, it was confirmed that the antigen-IgA complex which had been immuno-precipitated by the anti-IgA antibody in the urine from patients having IgA nephropathy always contained uromodulin without any exception.

From the above, it was found that uromodulin was contained in the antigen-IgA complex present in the urine from patients having IgA nephropathy, and therefore validity of the diagnosis of IgA nephropathy based on the sandwich method using an anti-uromodulin antibody and an anti-IgA antibody was confirmed.

Example 4

Detection of Renal Disease

—Detection of IgA-Uromodulin Complex in Urine Based on ELISA (2), Evaluation Using Different Test Group—

Except that a test group different from the test group of Example 1 was used, detection of IgA-uromodulin complex in urine based on ELISA was carried out in the same manner as Example 1. Meanwhile, as a measured value of the amount of complex, the amount of complex contained in a sample which was converted with reference to the standard by using color development value of the standard as prepared below (i.e., human IgA-human uromodulin complex) was used instead of the color development value.

(Preparation of Human IgA-Human Uromodulin Complex)

100 µl of 2 mg/ml Human IgA (manufactured by Cortex Corp.)/PBS-1 (10 mM potassium phosphate buffer, 150 mM NaCl, pH 7.8) and 100 µl of 1 mg/ml Human Tamm-Horsfall protein (manufactured by Cortex Corp.)/PBS-1 were admixed with each other, added with 20 µl of glutaraldehyde solution (manufactured by Taab Laboratories Equipment Limited) (0.5%/PBS-1), and mixed at 25° C. for 2 hours. The dialysate obtained after dialysis against PBS-1 was used as standard human IgA-human uromodulin complex.

Figure 10:
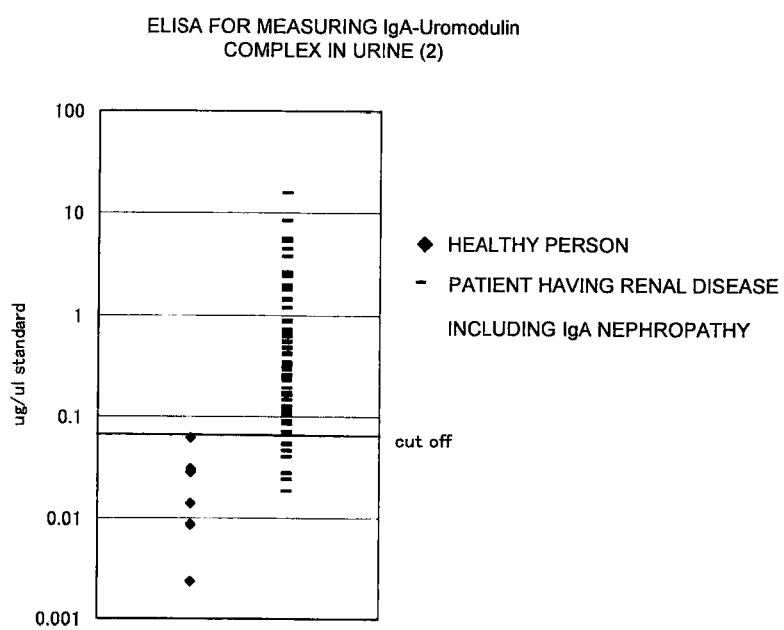
FIG. 10 is a distribution chart showing the measured values of the IgA-uromodulin complex in urine which is detected by ELISA.

The results of measuring IgA-uromodulin complex in urine from 74 cases of patients having a renal disease including 32 cases of patients having IgA nephropathy and 6 cases of healthy persons (normal person) are shown in FIG. 10.

By comparing the value obtained after subtraction of blank, results showing a significant difference between 74 cases of patients having a renal disease including 32 cases of patients having IgA nephropathy and 6 cases of healthy persons were obtained.

Figure 11:
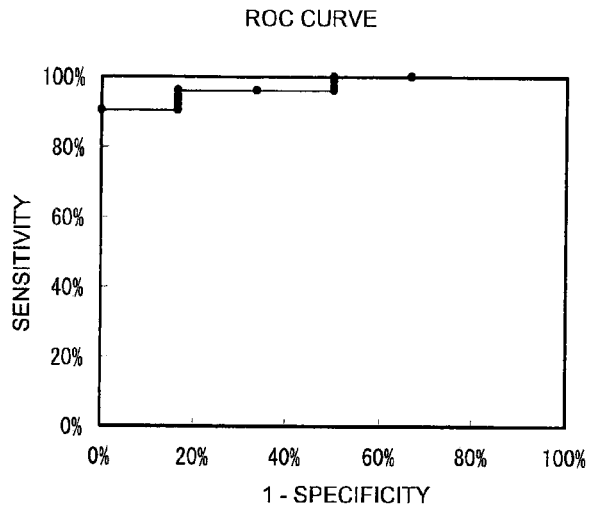
FIG. 11 is a diagram showing the results obtained from ROC analysis of the measured values of the IgA-uromodulin complex in urine which is detected by ELISA.

Furthermore, the ROC analysis was carried out for 74 cases of patients having a renal disease and 6 cases of healthy persons. The ROC curve is shown in FIG. 11. The cut-off value which was set to have the specificity of 100% was 0.064. The positive response ratio in 74 cases of patients having a renal disease and 6 cases of healthy persons, which was determined from the cut-off value, is shown in Table 5. As shown in Table 5, there were 67 cases showing a positive response (90.5%) out of 74 cases of patients having a renal disease compared to 0 (zero) case showing a positive response (0%) out of 6 cases of healthy persons, thus two groups can be clearly distinguished from each other. The sensitivity was 90.5%, specificity degree was 100%, and diagnosis efficiency was 91.3%.

TABLE 5

|  | Patient having a renal disease | Healthy person |
| --- | --- | --- |
| Number of samples | 74 | 6 |
| Number of positive response | 67 | 0 |
| Positive response ratio | 90.5% | 0.0% |

<Detection of IgA Nephropathy>

Figure 12:
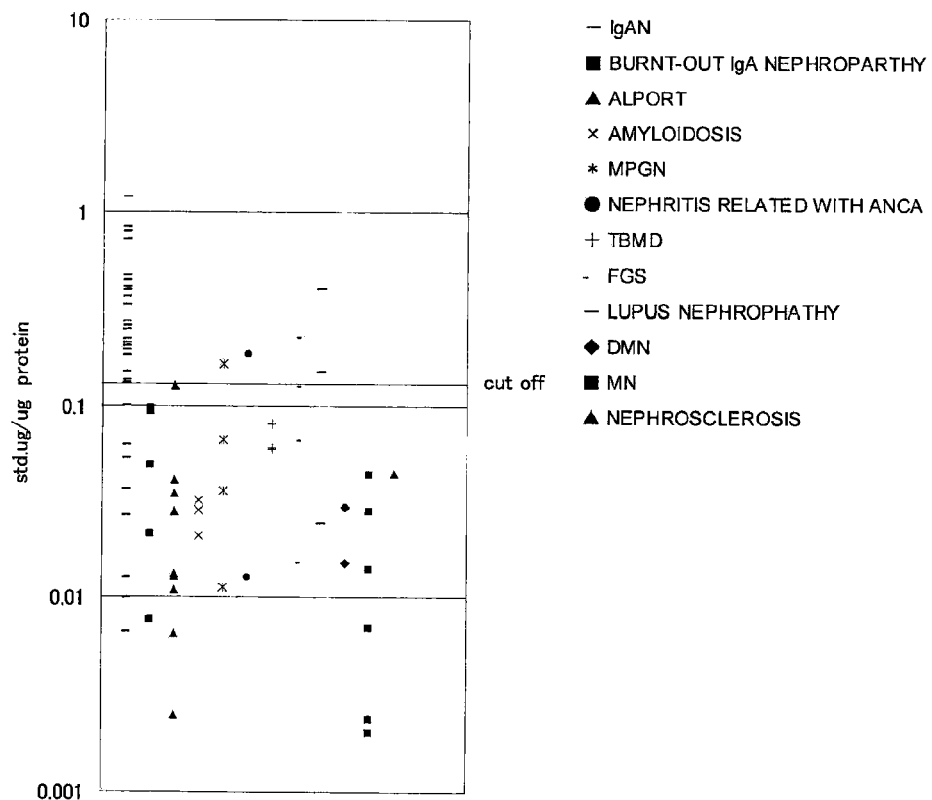
FIG. 12 is a distribution chart showing the measured values of the IgA-uromodulin complex in urine which is detected by ELISA, the measured values being corrected against the concentration of urinary proteins.

Next, for the sample in which the detected amount of the complex was the cut-off value above or more, urinary protein concentration in urine was quantified based on a pyrogallol red method. The detected amount of the complex, which has been detected from the above, was divided by the urinary protein concentration, and then the detection amount of the complex per amount of the urinary protein was calculated. The results are shown in FIG. 12. By comparing the detection amount of the complex per amount of the urinary protein, results demonstrating that 31 cases of patients having IgA nephropathy can be clearly distinguished from 36 cases of patients having a renal disease other than IgA nephropathy were obtained.

Figure 13:
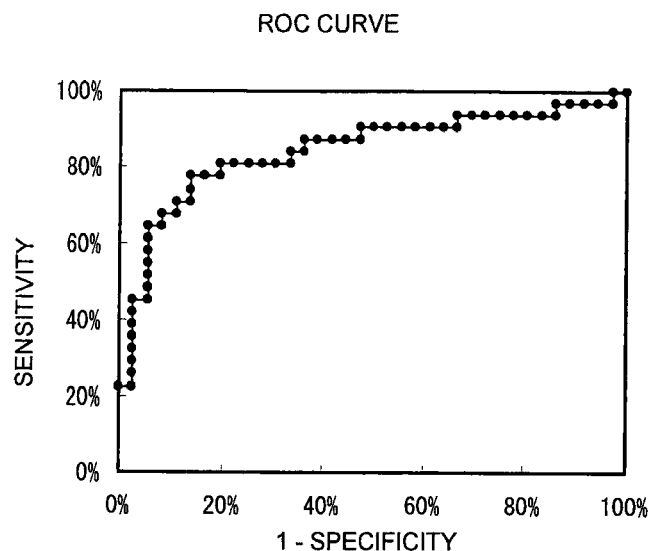
FIG. 13 is a diagram showing the results obtained from ROC analysis of the measurement values of the IgA-uromodulin complex in urine which is detected by ELISA, in which the measured values are corrected against the concentration of urinary proteins.

Furthermore, as a result of carrying out ROC analysis for 31 cases of patients having IgA nephropathy and 36 cases of patients having a renal disease other than IgA nephropathy, the ROC curve shown in FIG. 13 was obtained. The cut-off value calculated from the ROC curve was 0.13. The positive response ratio in 31 cases of patients having IgA nephropathy and 36 cases of patients having a renal disease other than IgA nephropathy, which was determined from the cut-off value, is shown in Table 6. As shown in Table 6, there were 24 cases showing a positive response (77.4%) out of 31 cases of patients having IgA nephropathy compared to 5 cases showing a positive response (13.9%) out of 36 cases of patients having a renal disease other than IgA nephropathy, thus two groups can be clearly distinguished from each other. The sensitivity was 77.4%, specificity degree was 86.1%, and diagnosis efficiency was 82.1%.

In particular, 8 cases of hereditary nephropathy (Alport) which is difficult to be distinguished from IgA nephropathy by clinical diagnosis and 4 cases of naturally cured IgA nephropathy (i.e., burnt-out IgA nephropathy) were all determined to be negative, and therefore it was found to be very effective for clinical diagnosis.

TABLE 6

|  | IgA nephropathy | Renal disease other than IgA nephropathy |
| --- | --- | --- |
| Number of samples | 31 | 36 |
| Number of positive response | 24 | 5 |
| Positive response ratio | 77.4% | 13.9% |

Reference Example 1

Detection of Renal Disease

—Detection of Uromodulin in Urine Based on ELISA—

An anti-human Tamm-Horsfall protein antibody (sheep, poly, manufactured by Biotrend Chemikalien GmbH) was labeled with peroxidase using Peroxidase Labeling Kit-NH2 (manufactured by Dojindo Molecular Technologies, Inc) according to the manufacturer's manual included in the kit (herein below, referred to as a "peroxidase-labeled anti-human Tamm-Horsfall protein antibody").

Figure 14:
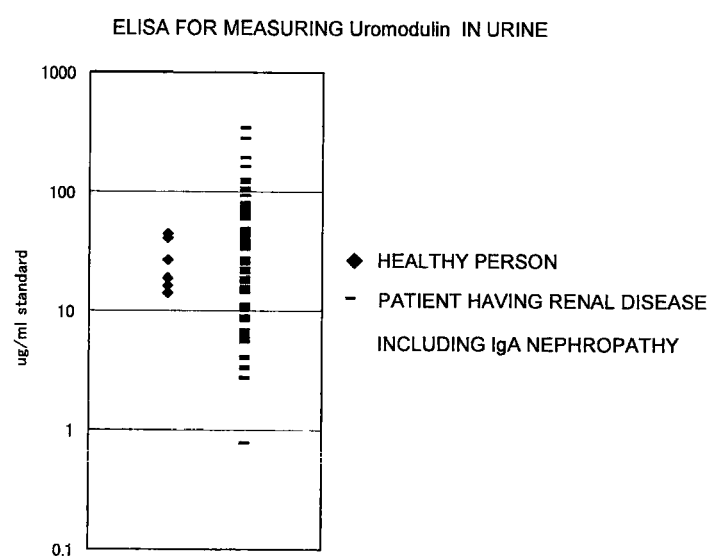
FIG. 14 is a distribution chart showing the measured values of human uromodulin in urine which is detected by ELISA.

The anti-Tamm-Horsfall cups obtained from the above were washed three times with the washing solution (50 mM Tris/HCl (pH 7.5), 150 mM NaCl and 0.01% Tween20) and added with urine samples, which were obtained by 1,000 to 10,000 times dilution using a sample dilution solution (50% N102 (manufactured by NOF Corp.), 50 mM Tris/HCl (pH 7.5), 150 mM NaCl and 2% Block Ace (manufactured by Dainippon Sumitomo Pharma Co., Ltd.)), in an amount of 50 µl/well for the reaction at room temperature for 1 hour. After washing three times with the washing solution (50 mM Tris/HCl (pH 7.5), 150 mM NaCl and 0.01% Tween20), peroxidase-labeled anti-human Tamm-Horsfall protein antibody diluted 1,000 times with Can Get Signal 2 (manufactured by Toyobo Inc.) was added in an amount of 50 µl/well, and the reaction was carried out at room temperature for 1 hour. After washing three times with the washing solution, 3,3',5,5'-Tetramethylbenzidine (TMB) Liquid Substrate System for ELISA (manufactured by Sigma Chemical Corporation) was added in an amount of 100 µl/well followed by reaction at room temperature for 30 minutes. After adding 0.5 M $H_2SO_4$ (100 µl/well) to terminate the reaction, OD (450 to 650 nm) was measured. Measurement results obtained from 74 cases of patients having a renal disease including 32 cases of patients having IgA nephropathy and 6 cases of healthy persons are shown in FIG. 14.

The values obtained after subtraction of blank were compared to each other. According to the results, 74 cases of patients having a renal disease including 32 cases of patients having IgA nephropathy cannot be distinguished from 6 cases of healthy persons.

Reference Example 2

Detection of IgA in Urine Based on ELISA

An anti-human immunoglobulin antibody (goat, poly anti-Human Ig's, manufactured by Biosource International Camarillo, Calif.) was diluted to the concentration of 10 µg/ml with 50 mM Tris/HCl (pH 7.5) and 0.15 M NaCl, and then added to PolySorp cups (manufactured by NUNC) (50 µl/well). The cups were placed in a humid box and coating was carried out overnight at 4° C. After the coating, they were washed three times with the washing solution (50 mM Tris/HCl (pH 7.5), 150 mM NaCl and 0.01% Tween20) followed by addition of the blocking solution (50% N102 (manufactured by NOF Corp.), 25 mM Tris/HCl (pH 7.5), 75 mM NaCl and 2% Block Ace (manufactured by Dainippon Sumitomo Pharma Co., Ltd.)) (150 µl/well). Thereafter, the blocking was carried out at room temperature for 2 hours or at 4° C. for one day or more (herein below, referred to as "anti-Ig's cups").

Figure 15:
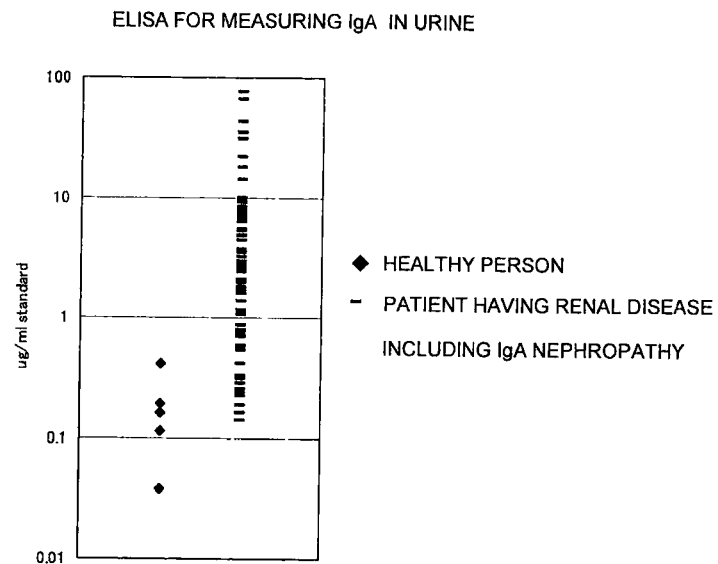
FIG. 15 is a distribution chart showing the measured values of human IgA in urine which is detected by ELISA.

The anti-Ig's cups were washed three times with the washing solution (50 mM Tris/HCl (pH 7.5), 150 mM NaCl and 0.01% Tween20) and added with urine samples, which were obtained by 1,000 times dilution using a sample dilution solution (50% N102 (manufactured by NOF Corp.), 50 mM Tris/HCl (pH 7.5), 150 mM NaCl and 2% Block Ace (manufactured by Dainippon Sumitomo Pharma Co., Ltd.)), in an amount of 50 µl/well for the reaction at room temperature for 1 hour. After washing three times with the washing solution (50 mM Tris/HCl (pH 7.5), 150 mM NaCl and 0.01% Tween20), HRP-labeled anti-human IgA antibody (manufactured by Zymed Labs) which has been diluted 1,000 times with Can Get Signal 2 (manufactured by Toyobo Inc.) was added in an amount of 50 µl/well, and the reaction was carried out at room temperature for 1 hour. After washing three times with the washing solution, 3,3',5,5'-Tetramethylbenzidine (TMB) Liquid Substrate System for ELISA (manufactured by Sigma Chemical Corporation) was added in an amount of 100 µl/well followed by reaction at room temperature for 30 minutes. After adding 0.5 M $H_2SO_4$ (100 µl/well) to terminate the reaction, OD (450 to 650 nm) was measured. Measurement results obtained from 74 cases of patients having a renal disease including 32 cases of patients having IgA nephropathy and 6 cases of healthy persons are shown in FIG. 15.

By comparing the value obtained after subtraction of blank, results showing a significant difference between 74 cases of patients having a renal disease including 32 cases of patients having IgA nephropathy and 6 cases of healthy persons were obtained, even though they were less dramatic than the results obtained from the measurement of uromodulin-IgA complex.

Figure 16:
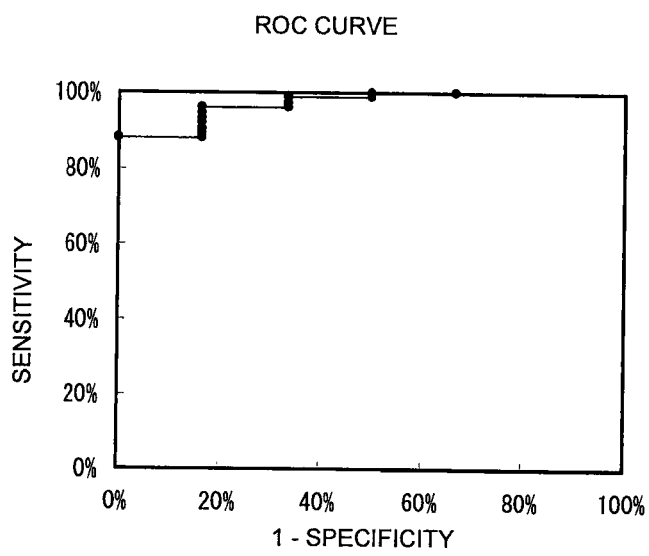
FIG. 16 is a diagram showing the results obtained from ROC analysis of the measured values of human IgA in urine which is detected by ELISA.

Furthermore, the ROC analysis was carried out for 74 cases of patients having a renal disease and 6 cases of healthy persons. The ROC curve is shown in FIG. 16. The cut-off value which was set to have the specificity of 100% was 0.418. The positive response ratio in 74 cases of patients having a renal disease and 6 cases of healthy persons, which was determined from the cut-off value, is shown in Table 7. As shown in Table 7, there were 64 cases showing a positive response (86.5%) out of 74 cases of patients having a renal disease compared to 0 (zero) case showing a positive response (0%) out of 6 cases of healthy persons, thus two groups can be clearly distinguished from each other. The sensitivity was 86.5%, specificity degree was 100%, and diagnosis efficiency was 87.5%.

TABLE 7

|  | Patient having a renal disease | Healthy person |
| --- | --- | --- |
| Number of samples | 74 | 6 |
| Number of positive response | 64 | 0 |
| Positive response ratio | 86.5% | 0.0% |

<Detection of IgA Nephropathy>

Figure 17:
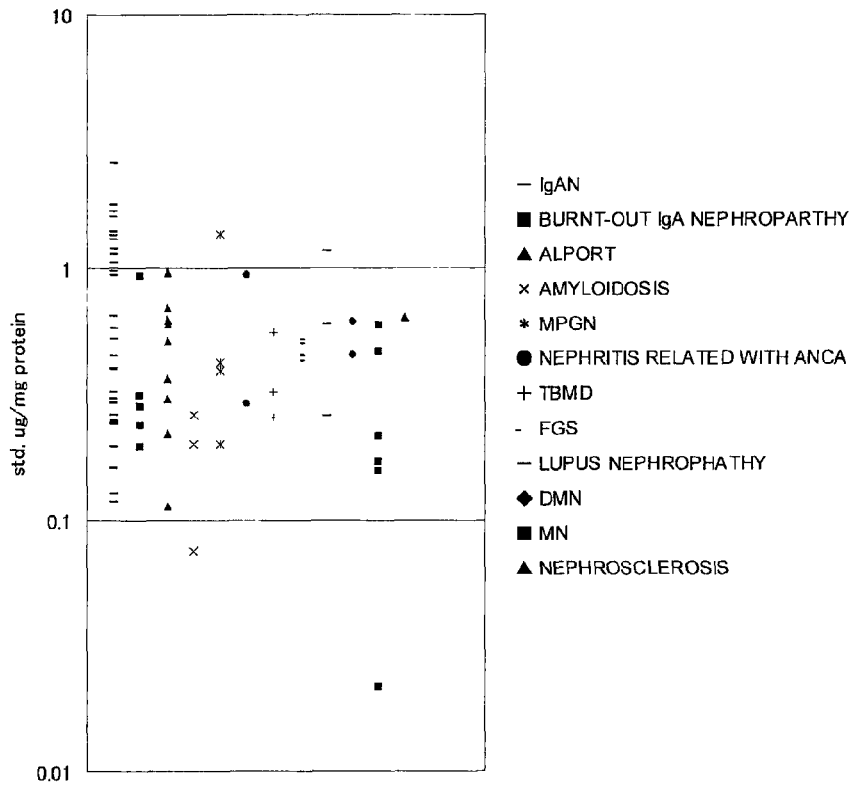
FIG. 17 is a distribution chart showing the measured values of human IgA in urine which is detected by ELISA, the measured values being corrected against the concentration of urinary proteins.
Figure 18:
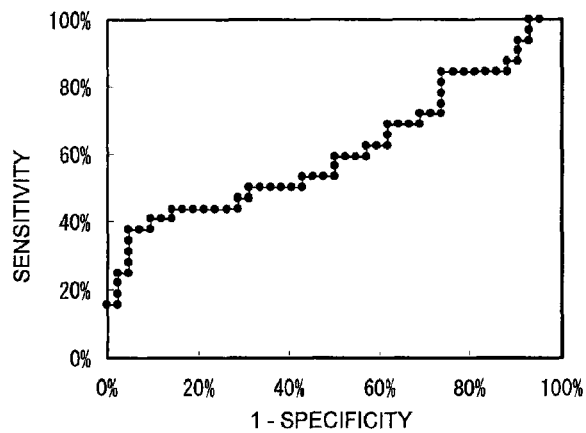
FIG. 18 is a diagram showing the results obtained from ROC analysis of the measurement values of human IgA in urine which is detected by ELISA, in which the measured values are corrected against the concentration of urinary proteins.

Next, for 74 cases of patients having a renal disease including 32 cases of patients having IgA nephropathy, urinary protein concentration in urine was quantified based on a pyrogallol red method. The detected amount of the IgA, which has been detected from the above, was divided by the urinary protein concentration, and then the detected amount of the IgA per amount of the urinary protein was calculated. The results are shown in FIG. 17. Furthermore, as a result of carrying out ROC analysis for 32 cases of patients having IgA nephropathy and 42 cases of patients having a renal disease other than IgA nephropathy, the ROC curve shown in FIG. 18 was obtained. As a result, it was found to be difficult to clearly distinguish 32 cases of patients having IgA nephropathy from 42 cases of patients having a renal disease other than IgA nephropathy based on the comparison of the detection amount of IgA per amount of the urinary proteins.

From the above, by detecting the complex of human IgA and human uromodulin present in urine, healthy persons (normal person) can be distinguished from patients having nephropathy.

In addition, by measuring the detected amount of the complex of human IgA and human uromodulin present in urine per the concentration of urinary proteins, IgA nephropathy and renal diseases other than IgA nephropathy can be distinguished from each other.

Meanwhile, when only human uromodulin present in urine is measured, healthy persons (normal person) cannot be distinguished from patients having nephropathy. When only human IgA present in urine is measured, healthy persons (normal person) can be distinguished from patients having nephropathy, but IgA nephropathy cannot be distinguished from a renal disease other than IgA nephropathy by measuring the detected amount of human IgA per the concentration of urinary proteins.

The invention claimed is:

1. An immunoglobulin A (IgA) nephropathy testing method, comprising detecting a complex of human uromodulin and human IgA in a sample derived from urine collected from a human subject, wherein an elevated amount of the complex detected in the sample as compared to the amount of the complex present in urine of healthy persons is used to correlate the existence of IgA nephropathy in the human subject.

2. The method according to claim 1, wherein detecting the complex comprises bringing the sample into contact with an antibody against human uromodulin and an antibody against human IgA.

3. The method according to claim 1, further comprising obtaining a ratio of the amount of the complex detected to the amount of urinary proteins in the sample.

4. The method according to claim 3, further comprising assessing the existence of IgA nephropathy on the basis of the ratio.

5. A renal disease testing method, comprising detecting a complex of human uromodulin and human IgA in a sample derived from urine collected from a human subject, wherein an elevated amount of the complex detected in the sample as compared to the amount of the complex present in urine of healthy persons is used to correlate the existence of a renal disease in the human subject, wherein the renal disease is IgA nephropathy, membranous nephropathy, systemic lupus erythematosus, focal glomerulosclerosis, minimal change nephrotic syndrome, or diabetic nephropathy.

6. The method according to claim 5, wherein detecting the complex comprises bringing the sample into contact with an antibody against human uromodulin and an antibody against human IgA.

7. An IgA nephropathy testing method, comprising:
    detecting a complex of human uromodulin and human IgA in a sample derived from urine collected from a human subject;
    assessing the existence of a renal disease in the human subject on the basis of at least one of the amount of the complex detected or the amount of urinary proteins in the sample; and
    assessing whether the renal disease is IgA nephropathy on the basis of a ratio of the amount of the complex detected to the amount of urinary proteins in the sample.

8. The method according to claim 1, wherein detecting the complex comprises an immunochemical method using an antibody against human uromodulin and an antibody against human IgA.

9. The method according to claim 8, wherein the immunochemical method is a sandwich method.

10. A method of detecting a complex of human uromodulin and human IgA, the method comprising bringing a sample derived from urine collected from a human subject into contact with an antibody against human uromodulin and an antibody against human IgA.

11. The method according to claim 10, wherein the complex is detected by an immunochemical method using the antibody against the human uromodulin and the antibody against the human IgA.

12. The method according to claim 11, wherein the immunochemical method is a sandwich method.

13. The method according to claim 10, wherein the human subject is a person who has developed a renal disease, a person who is suspected to have developed a renal disease, or a person who has a possibility of developing a renal disease.

14. The method according to claim 13, wherein the renal disease is IgA nephropathy.

15. A test kit for a renal disease selected from the group consisting of IgA nephropathy, membranous nephropathy, systemic lupus erythematosus, focal glomerulosclerosis, minimal change nephrotic syndrome, and diabetic nephropathy, comprising:
    an antibody against human uromodulin and
    an antibody against human IgA.

16. The test kit according to claim 15, wherein the renal disease is IgA nephropathy.

* * * * *